United States Patent [19]

Dastur

[11] 4,173,584

[45] Nov. 6, 1979

[54] NOVEL CYCLOPENTANONE DERIVATIVES AS FLAVOR- AND ODOR-MODIFYING INGREDIENTS

[75] Inventor: Khurshid P. Dastur, Satigny, Switzerland

[73] Assignee: Firmenich SA, Geneva, Switzerland

[21] Appl. No.: 793,287

[22] Filed: May 3, 1977

[30] Foreign Application Priority Data

May 13, 1976 [CH] Switzerland ................... 5995/76

[51] Int. Cl.$^2$ ........................................... C07C 49/28
[52] U.S. Cl. ............................. 260/586 R; 131/17 R; 252/522; 252/174.11; 260/586 C; 424/70; 424/76; 426/538; 426/593; 426/594; 426/597
[58] Field of Search ................................... 260/586 R

[56] References Cited

PUBLICATIONS

Voitsekhovskaya et al, "Chem. Ab.", 66:94712w, (1967), [Zh. Org. Khim, 3(1), 18–24, (1967) (Russ)].
Gault et al, "Chem. Abstracts", 52:4509b, (1958), [Bull. Soc. Chim. France, 1957, 1064–1069].

*Primary Examiner*—Norman Morgenstern
*Attorney, Agent, or Firm*—Pennie & Edmonds

[57] ABSTRACT

Novel cyclopentanone derivatives are found to be useful as flavor and odor modifying ingredients. The new compounds are particularly useful in the preparation of perfumes and perfumed products as well as for the aromatization of foodstuffs and beverages.

4 Claims, No Drawings

NOVEL CYCLOPENTANONE DERIVATIVES AS FLAVOR- AND ODOR-MODIFYING INGREDIENTS

BACKGROUND OF THE INVENTION

Certain cyclopentanone derivatives are already known in the art of perfumery and in that of flavours. Some of them represent very valuable materials whose utility in the field is well established. Jasmone, methyl jasmonate and methyl dihydrojasmonate for instance [see S. Arctander, Perfume and Flavor Chemicals, Montclair N.J. (1969) USA; Sect. 1788, 2093 and 2076, respectively], are known to possess floral, jasmin-like odoriferous notes of great elegance. Analogous properties are shown by 2-n-hexyl- and 2-n-pentyl-cyclopentanone [S. Arctander, op. cit.; Sect. 1659 and 1534, respectively], whereas scientific literature reports that 2,2,5-trimethyl-cyclopentanone, 2,2,5,5-tetramethyl-cyclopentanone and 2-methyl-2,5,5-tripropyl-cyclopentanone possess weak odours of minty, camphery and anise type of no recognized utility for the art.

THE INVENTION

We have now surprisingly discovered that compounds of formula

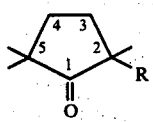

I wherein symbol R represents an alkyl radical comprising from 4 to 6 carbon atoms, possess an original fruity, slightly green flowery odour character reminiscent of the scent of peaches or apricots. The present invention relates consequently to a process for imparting, modifying or enhancing the odoriferous properties of perfumes or perfumed products, which process comprises the step of adding to said materials an effective amount of a compound of formula I. A further object of the invention is to provide a process for the aromatization of foodstuffs, feedstuffs, beverages, pharmaceutical preparations and tobacco products which comprises adding thereto a flavour modifying amount of a compound of formula I.

The invention further relates to a perfume or flavouring composition containing as one of its active ingredients a compound of formula I.

Finally, the present invention relates to a flavoured or perfumed article containing as flavouring or, respectively, perfuming ingredient a compound of formula I.

PREFERRED EMBODIMENTS OF THE INVENTION

As stated above symbol R represents an alkyl radical comprising from 4 to 6 carbon atoms. Preferentially, said alkyl radical is linear and represents a butyl, a pentyl or a hexyl radical. Typically, compounds of formula I define compounds such as
- 2,5,5-trimethyl-2-butyl-cyclopentanone,
- 2,5,5-trimethyl-2-pentyl-cyclopentanone and
- 2,5,5-trimethyl-2-hexyl-cyclopentanone.

Owing to their specific organoleptic properties, compounds I can find a utility for the reconstruction of fresh, flowery and fruity notes. Their peach- or apricot-like scent enables the manufacture of original perfume compositions of modern character. It should be emphasized that such an effect cannot be achieved by the utilization of the above cited prior known compounds.

In actual experience, the novel compounds of the invention are particularly suitable for the manufacture of perfume compositions of chypre, fruity, green, fourgere or flowery type. For instance, 2,5,5-trimethyl-2-pentyl-cyclopentanone develops in the said perfume compositions a very natural fruity scent reminiscent of the odour developed by peaches, occasionally accompanied by a green note typical in cress like plants.

The perfume compositions containing compounds I can suitably be employed for the compounding of fine perfumes as well as for the perfuming of technical products such as soaps, detergents, house-hold materials or shampoos and cosmetics.

The proportions in which the cyclopentanones of the invention can produce the desired perfuming effects can vary within wide limits. Typically, these proportions are of about 0.1 to 10, or even 20% or more by weight of compounds I based on the total amount of the perfumed article into which they are incorporated. Preferentially, these proportions are from about 1 to about 10%.

In the field of aromatization, compounds I present a peachy, bergamot, fatty, floral, lactonic gustative character and consequently their use enables the manufacture of flavour compositions of different nature, eminently of fruity character. They also develop sweet, fermented or mushroomlike aromatic notes.

Preferred concentrations are of between about 0.5 to 50 ppm by weight based on the total weight of the flavoured materials.

The proportions indicated above are not deemed to be interpreted restrictively and values lower or higher than the above given limits can be used whenever special effects are desired.

As used throughout this specification, the term "foodstuff" includes also articles such as tea, coffee or chocolate.

A further advantage of the compounds of the invention is represented by their accessibility. In fact, their preparation can be achieved by starting from easily available commercial materials. In certain instances, the starting material is currently available as intermediate in the syntheses of industrially manufactured products. Such is for instance the case of 2-pentyl-cyclopentanone, used for the manufacture of 2,5,5-trimethyl-cyclopentanone, said starting material being an intermediate in the synthesis of methyl dihydrojasmonate—see Swiss Pat. No. 382,731.

The preparation of compounds I can be effected according to conventional methods, by treating for example a derivative of cyclopentanone of formula

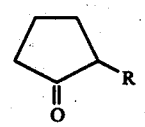

II wherein symbol R has the above given meaning, with an appropriate alkylating agent.

As exemplification, an experimental description of the method followed for the synthesis of certain compounds of formula I is given hereinbelow.

2,5,5-Trimethyl-2-pentyl-cyclopentanone 18.7 g of sodium hydride were added to a solution of 30 g of 2-pentyl-cyclopentanone in 500 ml of tetrahydrofurane, whereupon 100 g of methyl iodide in 100 ml of tetrahydrofurane were added thereto under stirring within about 15 minutes. The reaction mixture is kept during 20 hours at 65° C. and finally cooled to room temperature. After addition of 20 ml of water, followed by 300 ml of ether, the organic phase was separated, dried over $Na_2SO_4$ and evaporated. A distillation gave 34 g (92% yield) of the desired product having b.p. 35° C./0.1 Torr.

IR (film): 1730, 1460, 1020 and 890 cm$^{-1}$.
NMR ($CCl_4$):0.97 (6H, s); 1.02 (3H, s) $\delta$ ppm.
MS: M$^+$=196.

The product thus obtained can be used according to the invention without further purification.

Starting from 2-butyl-cyclopentanone and 2-hexylcyclopentanone respectively, and by following the same procedure as indicated above, the following two compounds were obtained:

2,5,5-trimethyl-2-butyl-cyclopentanone

IR (film): 1735, 1460 and 887 cm$^{-1}$.
NMR ($CCl_4$): 0.99 (6H, s); 1.04 (3H, s) $\delta$ ppm, and

2,5,5-trimethyl-2-hexyl-cyclopentanone

IR (film): 1735, 1460 and 887 cm$^{-1}$.
NMR ($CCl_4$): 0.97 (6H, s); 1.03 (3H, s); 1.30 (10H, broad s) $\delta$ ppm.

The invention is better illustrated by but not limited to the following examples.

EXAMPLE 1

Perfume Compositions

A base perfume composition of fruity type is prepared by mixing together the following ingredients (parts by weight):

| | |
|---|---|
| γ-Undecalactone 10%* | 560 |
| Phenylethanol | 200 |
| Methyldihydrojasmonate | 60 |
| 2-Ethyl-hexanol | 35 |
| 2-Methyl-4-n-propyl-1,3-oxathiane** 1%* | 30 |
| δ-Dodecalactone | 25 |
| γ-Decalactone | 20 |
| cis-Hex-3-en-1-ol 10%* | 20 |
| Menthyl acetate | 10 |
| γ-Nonalactone | 10 |
| Total | 970 |

*in diethyl phthalate
**See German Offen. No. 25 34 162

The said perfume base possesses a fruity odour reminiscent of that of peach and finds a utility namely in the preparation of beauty creams.

By adding to 97 g of it 3 g of 2,5,5-trimethyl-2-pentyl-cyclopentanone, there was obtained a novel composition having a more pleasant and more natural odour than the base composition.

EXAMPLE 2

Perfumed Detergent 2 g of 2,5,5-trimethyl-2-pentyl-cyclopentanone were added to 1 kg of commercial detergent powder base. The thus perfumed article possessed an elegant, jasmin-like, lactonic odour of powdery character. This type of fragrance is particularly difficult to achieve by the use of currently available lactones, such as nonalactone and γ-undecalactone, owing to their poor stability in alkaline media.

The fragrance was very stable and no odour modification was observed after storage of a sample of the perfumed detergent for 1 month at 40° C. and 3 months at room temperature. 2,5,5-Trimethyl-2-pentyl-cyclopentanone was used to perfume standard articles in the concentrations given below. The stability and the colour of the perfumed articles is indicated in the following scheme:

| Article | Concentration by weight | Temperature [°C.] | Performances stab./colour |
|---|---|---|---|
| Eau-de-Cologne | 5% in ethanol | 22 | S/N* |
| | | 40 (1 month) | S/N |
| | | 0 | S/N |
| Soap | 1% | 22 | S/N |
| | | 40 (1 month) | S/N |
| Non-fatty cream | 0.2% | 22 | S/N |
| Shampoo | 0.2% | 22 | S/N |
| | | 40 (1 month) | S/N |
| Deodorizer | 0.2% | 22 | S/N |

*S = stable
N = normal

The perfume ingredient proven also stable to prolonged UV irradiation.

EXAMPLE 3

Apricot Juice

A commercial apricot juice was flavoured with 5 ppm of 2,5,5-trimethyl-2-pentyl-cyclopentanone and the thus obtained beverage (test solution) was tasted by comparison with the unflavoured material (control solution). A group of experts declared that the test solution possessed a more fruity, more fresh apricot character than the control solution.

By proceeding in analogous manner, the following materials were flavoured by using the given quantities of 2,5,5-trimethyl-2-pentyl-cyclopentanone. The taste observed is described by comparison with the respective unflavoured material.

| | | |
|---|---|---|
| Apricot jam: | 10 ppm | more odour and flavour impact and a fresher apricot character |
| Peach juice: | 5 ppm | improved taste, more rounded peach character and a fresher fruit note. |
| Passion fruit juice: | 3 ppm | improved fruity character, sweeter and fresher top note. |

What we claim is:

1.

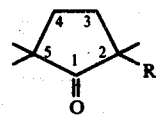

wherein symbol R represents an alkyl radical comprising from 4 to 6 carbon atoms.

2. A comound according to claim 1 wherein symbol R represents a linear alkyl radical.

3. A compound according to claim 2 wherein symbol R represents n-butyl, n-pentyl or n-hexyl.

4. 2,5,5-Trimethyl-2-pentyl-cyclopentanone.

UNITED STATES PATENT AND TRADEMARK OFFICE
CERTIFICATE OF CORRECTION

PATENT NO. : 4,173,584
DATED : November 6, 1979
INVENTOR(S) : Khurshid Dastur

It is certified that error appears in the above-identified patent and that said Letters Patent are hereby corrected as shown below:

Column 1, line 66, "reconstruction" should read --reconstitution--.

Column 2, lines 7 and 8, "fourgere" should read --fougere--.

Column 4, line 24, "proven" should read --proved--.

Column 4, line 52, "1." should read --1. A compound of formula--.

Signed and Sealed this

Fifth Day of August 1980

[SEAL]

Attest:

SIDNEY A. DIAMOND

Attesting Officer     Commissioner of Patents and Trademarks